United States Patent [19]

Kennedy

[11] 4,129,946
[45] Dec. 19, 1978

[54] DENTAL CROWN FORM

[75] Inventor: Brian G. Kennedy, Claremont, Calif.

[73] Assignee: Unitek Corporation, Monrovia, Calif.

[21] Appl. No.: 769,549

[22] Filed: Feb. 17, 1977

[51] Int. Cl.$^2$ ................................................ A61C 5/12
[52] U.S. Cl. ............................................ 32/63; 32/12
[58] Field of Search ................................ 32/63, 12, 8

[56] References Cited

U.S. PATENT DOCUMENTS

| 297,703 | 4/1884 | Matteson | 32/42 |
| 1,265,581 | 5/1918 | Zurbrigg | 32/63 |
| 2,629,172 | 2/1953 | Keiger | 32/63 |
| 3,421,222 | 1/1969 | Newman | 32/63 |

Primary Examiner—Robert Peshock
Attorney, Agent, or Firm—Christie, Parker & Hale

[57] ABSTRACT

A dental crown form or strip crown for holding and shaping a body of composite resin material being applied to an anterior tooth requiring restoration. The crown form is a thin hollow body with an interior surface conforming to the shape of a natural tooth. A tab is integrally formed at the base or gingival end of the crown form, and the tab extends away from the base to provide a gripping handle for the crown and a surface for displaying a designation of the tooth of intended use. A flange is integrally formed around the base to strengthen and rigidify the crown form which is preferably made of co-polyester plastic.

5 Claims, 7 Drawing Figures

DENTAL CROWN FORM

BACKGROUND OF THE INVENTION

A significant recent advance in the science of dental materials has been the availability of composite-resin plastic materials such as disclosed in U.S. Pat. Nos. 3,629,187, 3,709,866, 3,835,090, and 3,845,009. These materials are useful in restoring the natural shape and function of a tooth which has been damaged by decay or fracture resulting in loss of some of the natural tooth structure.

The damaged tooth is prepared by conventional drilling and grinding techniques to remove carious material and to provide anchorage for the restoration material. The composite resin is then applied in a viscous state to the prepared tooth and allowed to set to a hard condition. These restorative materials are useful on either primary or permanent teeth, and are principally applied to anterior teeth which do not bear the heavy crushing loads to which the occlusal surfaces of molar teeth are subjected during chewing of food.

Crown forms or so-called strip crowns are known, and these forms serve as molds to hold and shape the restoration material during application to and setting or curing on the prepared tooth. Typical commercially available crown forms are a thin shell-like hollow body shaped to correspond to a specific natural tooth and made of cellulose-acetate materials. A generally cylindrical extension is typically formed at the gingival or base end of the body, and this extension and the body are trimmed as necessary to provide a good fit on the prepared tooth.

The crown form is partially filled with the compositeresin restorative material, and is then fitted over the prepared tooth to pack the composite material against the tooth and the interior surface of the form. Any surplus material is vented and removed, and the remaining material is molded by the form into a natural tooth-crown shape and supported in this shape until the material hardens. The wall of the form is then cut, and the form is stripped away from the tooth and restoration material. The restoration is completed by conventional grinding and polishing to insure conformance to a natural tooth shape.

Several problems are encountered in the use of these conventional "strip" crowns. The cellulose-acetate material used in prior-art crowns is prone to slump and deform during storage, requiring special packaging techniques and possible re-shaping prior to use. This material also tends to adhere to the hardened restoration, and is difficult to peel from the restoration in a single operation. These crowns are also awkward and difficult to hold without distortion when being partially filled with the restoration material and during installation on the prepared tooth. Prior-art crowns are further typically unmarked as to the tooth of intended use, leading to a problem of sorting and identifying any units which have been removed from marked storage containers.

The crown form of this invention is an improvement over known strip crowns in both shape and material. The new crown form is made of a co-polyester plastic which has good shape-retaining properties, and is readily stripped as a unit from the cured restoration material. An important feature is the provision of an integrally molded tab at the gingival end of the crown form to serve as both a handle and a flat surface for displaying tooth-identification information. A continuous outwardly extending flange is also formed at the gingival end to strengthen and rigidify the crown form.

SUMMARY OF THE INVENTION

Briefly stated, this invention relates to an improvement in a dental crown form for holding and shaping a restoration material being applied to a prepared damaged tooth, the crown form being a hollow body with an incisal end, an open gingival end, and an interior surface conforming in shape to a desired final restored shape of the damaged tooth. The improvement includes provision of a tab which is secured to the crown form adjacent the gingival end, and which extends transversely therefrom to provide a handle by which the crown form can be held during insertion of the restoration material and when the crown form is installed on the damaged tooth.

Preferably, the tab is integrally formed with the crown form, and extends perpendicularly to an occlusoapical axis of the crown form. The material used to make the crown-form body and tab is preferably a transparent co-polyester plastic, and a marking means on the tab designates a specific tooth on which the crown form is to be used. The crown form also preferably includes an outwardly extending flange formed around the periphery of the open gingival end to strengthen the crown form and prevent distortion of the inner surfaces which form a mold for the restoration material.

DESCRIPTION OF THE PREFERRED EMBODIMENT

Figure 1:
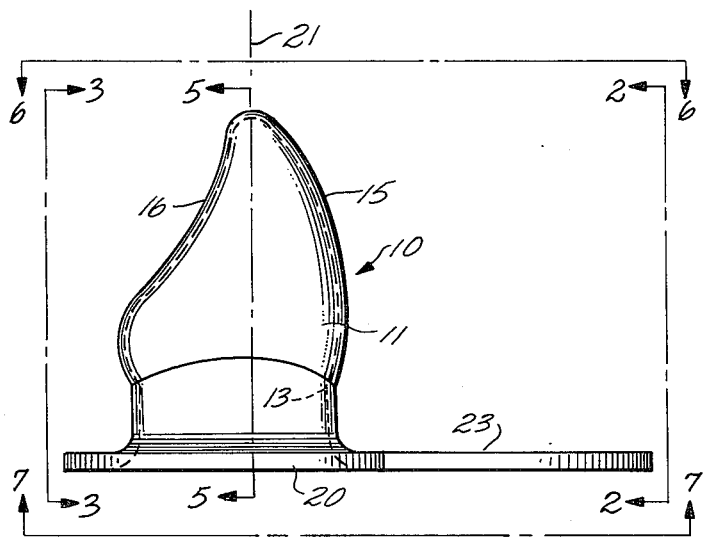
FIG. 1 is a side elevation of a crown form according to the invention.
Figure 2:
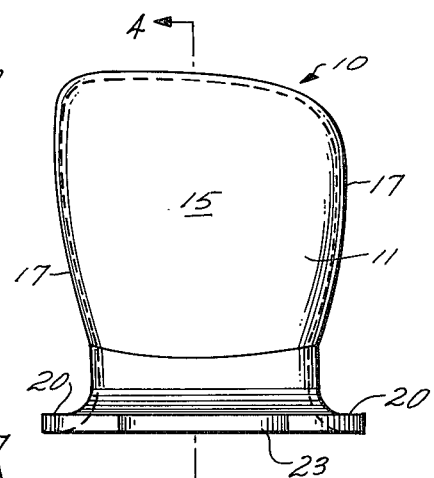
FIG. 2 is a front or labial view on line 2—2 of FIG. 1.
Figure 3:
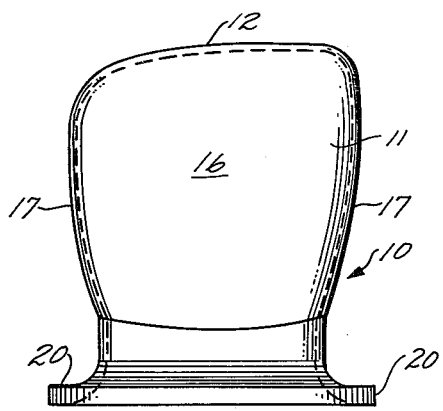
FIG. 3 is a rear or lingual view of the crown form on line 3—3 of FIG. 1.
Figure 4:
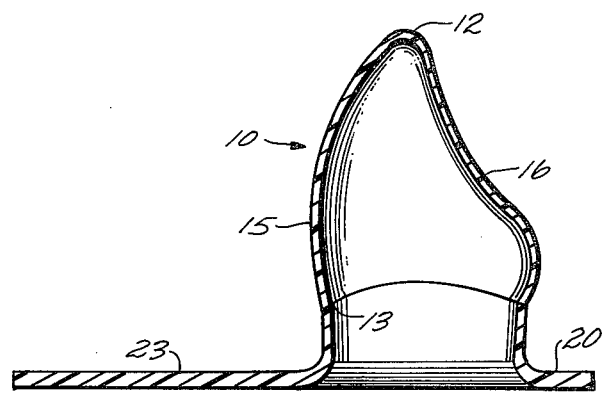
FIG. 4 is a side sectional elevation on line 4—4 of FIG. 2.
Figure 5:
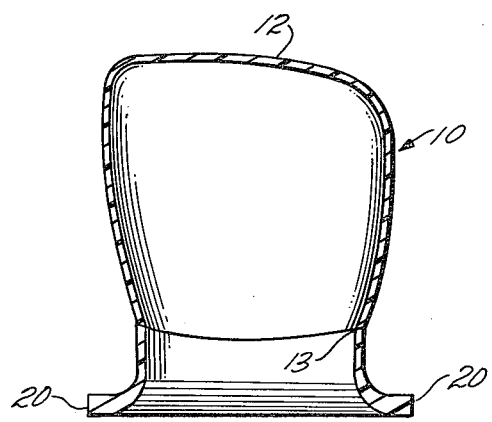
FIG. 5 is a front or labial sectional elevation on line 5—5 of FIG. 1.
Figure 6:
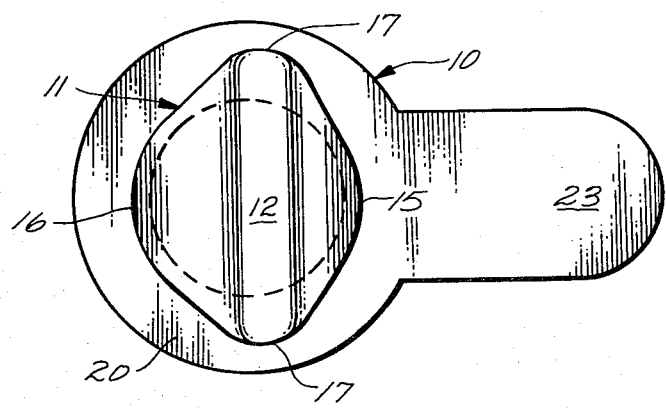
FIG. 6 is a top or incisal view on line 6—6 of FIG. 1.
Figure 7:
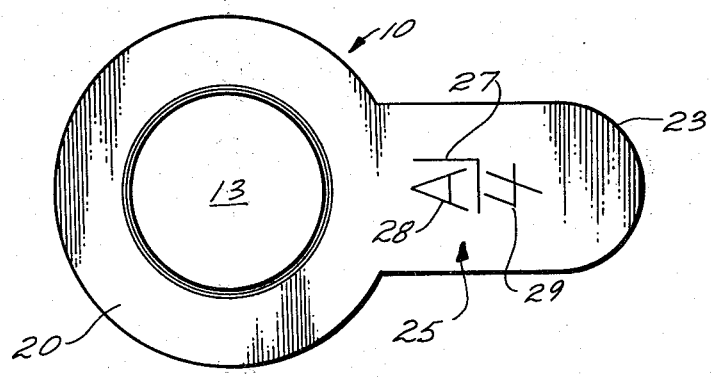
FIG. 7 is a bottom view on line 7—7 of FIG. 1.

Referring to the drawings, a strip crown or dental crown form 10 according to the invention includes a thin shell-like tooth form 11 having the shape of a specific tooth in the dental arch. For example, different tooth forms are provided for the central and lateral incisor teeth in the upper and lower jaws. To be useful on natural teeth of different sizes, each tooth form is typically provided in several different widths and lengths.

Tooth form 11 is hollow and has a closed incisal end 12 and an open gingival end 13. The thickness of the tooth-form sidewall is preferably about 0.010 inch ± 0.003 inch. The tooth form has a labial surface 15, linqual surface 16, and interproximal side surfaces 17, and these surfaces are contoured to match the shape of the specific tooth on which the crown form is to be used.

A continuous outwardly extending flange 20 is integrally formed at the open gingival end of the tooth form. As shown in the drawings, the flange extends substantially perpendicularly to an occluso-apical axis 21 of the tooth form.

An elongated tab 23 is integrally formed with the flange 20 at the base of the tooth form, and extends labially away from labial surface 15 and substantially perpendicularly to the occluso-apical axis of the tooth form. The flange and tab are about 0.020 inch thick, and are therefore substantially more rigid than the thinner tooth form. The tab is preferably about ¼-inch long and 3/16-inch wide to provide a gripping surface for the crown form.

A marking means 25 on the undersurface of tab 23 designates the tooth on which the crown form is to be used. The marking means is conveniently formed as a set of raised characters which are impressed in the tab at the time the crown form is molded. The marking means preferably includes a standard Palmer notation consisting of a right angle symbol 27 designating a specific half of one of the two dental arches, and a letter or number 28 designating a specific tooth within that arch section. An additional letter or number 29 is positioned below the Palmer-notation symbol to designate the size of the crown form.

The raw material used to make the crown form is preferably a sheet of co-polyester plastic (Eastman A-150 material is satisfactory) with a thickness of about 0.030 inch. A material of this type is satisfactory for thermoforming into the final integral crown form. The co-polyester material has proved superior to prior-art acetate materials in that it severs and peels cleanly when the crown form is removed from a restored tooth, and does not tend to fracture or break into small pieces which must be individually removed from the restored tooth.

Stiffening flange 20 substantially strengthens the relatively thin structure of the tooth form, and prevents unwanted deformation of the form during storage and handling. The use of a co-polyester plastic also contributes to the structural integrity of the crown form as this material does not deform and slump as readily as previously used cellulose-acetate material.

In use, the dentist selects a crown form of the proper size for the tooth being restored, and mixes a composite-resin material which is then loaded into the interior of the tooth form. Tab 23 provides a convenient handle for holding the crown form during the loading operation, and during subsequent installation of the crown form on the tooth being restored. The flange and gingival end of the crown form may also be trimmed as necessary to fit properly on the prepared tooth.

As the crown form is being positioned on the prepared tooth, the condition of the composite-resin material can be observed through the transparent sidewall of the tooth form, and the dentist can insure that there are no voids or air bubbles in the restorative material. When the crown form has been properly positioned, it is left in place until the composite-resin material had set. If a photopolymerizable material is being used, the restorative material may be irradiated (typically with ultraviolet light) through the transparent sidewall of the tooth form.

Setting of the composite-resin material is typically complete within 5 to 10 minutes, and a portion of the crown-form flange and sidewall are then severed with a blade or wheel, enabling the crown form to be stripped off the restored tooth as a unit. The crown form is a one-use device, and is normally discarded upon completion of the restoration process.

There has been described an improved crown form which serves as a mold or matrix for shaping and positioning a composite-resin material used to restore a damaged tooth. The crown form is inexpensive to produce, and has significant advantages over prior-art strip crowns in that the new crown form is much easier to handle, load, and position on the tooth, and is not subject to the deformation problems which characterize earlier designs. The inclusion of a tab at the base of the crown form not only provides a convenient gripping handle, but also enables inclusion of tooth and size information directly on the crown form.

What is claimed is:

1. In a dental crown form for holding and shaping a restoration material being applied to a prepared damaged tooth, the crown form being a hollow body with an incisal end, an open gingival end, and interior labial, lingual, and interproximal surfaces forming a continuous sidewall conforming in shape to a desired final restored state of the damaged tooth, the improvement comprising a tab secured to the crown form adjacent the gingival end of the body to provide a handle by which the crown form can be held during insertion of the restoration material and when the crown form is installed on the damaged tooth, the tab being integrally formed with the hollow body of the crown form, and extending substantially perpendicularly to an occluso-apical axis of the crown form.

2. The improvement defined in claim 1 wherein the hollow body and tab are an integrally molded body of substantially transparent co-polyester plastic.

3. The improvement defined in claim 2 wherein the tab includes marking means designating a specific tooth on which the crown form is to be used.

4. The improvement defined in claim 1 wherein an outwardly extending flange is integrally formed around the periphery of the open gingival end of the crown form to strengthen the open end.

5. The improvement defined in claim 4 wherein the crown form, tab and flange are an integrally molded body of substantially transparent co-polyester plastic, the tab and flange being substantially coplanar, and wherein the tab includes marking means designating a specific tooth on which the crown form is to be used.

* * * * *